United States Patent
Mueller

(10) Patent No.: US 8,439,911 B2
(45) Date of Patent: May 14, 2013

(54) COMPACT JAW INCLUDING THROUGH BORE PIVOT PIN

(75) Inventor: Peter Michael Mueller, Frederick, CO (US)

(73) Assignee: Coviden LP, Mansfield, MA (US)

(*) Notice: Subject to any disclaimer, the term of this patent is extended or adjusted under 35 U.S.C. 154(b) by 499 days.

(21) Appl. No.: 12/556,427

(22) Filed: Sep. 9, 2009

(65) Prior Publication Data
US 2011/0060333 A1    Mar. 10, 2011

(51) Int. Cl.
    *A61B 18/14* (2006.01)
(52) U.S. Cl.
    USPC .......................................................... 606/51
(58) Field of Classification Search ............... 606/45–52
    See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D348,930 S | 7/1994 | Olson |
| 5,496,317 A | 3/1996 | Goble et al. |
| 5,496,347 A | 3/1996 | Hashiguchi et al. |
| 5,540,685 A | 7/1996 | Parins et al. |
| D384,413 S | 9/1997 | Zlock et al. |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| 6,500,176 B1 * | 12/2002 | Truckai et al. ................... 606/51 |
| 6,620,161 B2 * | 9/2003 | Schulze et al. ................... 606/51 |
| D493,888 S | 8/2004 | Reschke |
| D496,997 S | 10/2004 | Dycus et al. |
| D499,181 S | 11/2004 | Dycus et al. |
| D509,297 S | 9/2005 | Wells |
| D525,361 S | 7/2006 | Hushka |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Tinkcler L.F., "Combined Diathermy and Suction Forceps", Feb. 6, 1967, British Medical Journal Feb. 6, 1976, vol. 1, nr. 5431 p. 361, ISSN: 0007-1447.

(Continued)

*Primary Examiner* — Michael Peffley

(57) ABSTRACT

An end effector assembly for use with a forceps includes a pair of jaw members, a knife assembly, and one or more cam assemblies. One or more of the jaw members are moveable relative to the other about a pivot from a first, open position to a second, closed position. One or more of the jaw members include a knife channel. The pivot includes a bore. The knife assembly includes a knife blade and an actuation shaft. The knife blade is disposed distally relative to the pivot. The actuation shaft is configured for slidable translation through the bore to allow selective advancement of the knife blade through the knife channel. The one or more cam assemblies are operably coupled to the one or more moveable jaw members and are actuatable to move the one or more jaw members from the first to second position for grasping tissue therebetween.

23 Claims, 10 Drawing Sheets

U.S. PATENT DOCUMENTS

| | | | |
|---|---|---|---|
| 7,083,618 B2 | 8/2006 | Couture et al. | |
| 7,101,371 B2 | 9/2006 | Dycus et al. | |
| D531,311 S | 10/2006 | Guerra et al. | |
| D533,942 S | 12/2006 | Kerr et al. | |
| 7,150,097 B2 | 12/2006 | Sremcich et al. | |
| 7,150,749 B2 | 12/2006 | Dycus et al. | |
| D535,027 S | 1/2007 | James et al. | |
| 7,156,846 B2 | 1/2007 | Dycus et al. | |
| D541,418 S | 4/2007 | Schechter et al. | |
| D541,938 S | 5/2007 | Kerr et al | |
| 7,232,440 B2 * | 6/2007 | Dumbauld et al. | 606/51 |
| 7,252,667 B2 | 8/2007 | Moses et al. | |
| 7,255,697 B2 | 8/2007 | Dycus et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,442,194 B2 | 10/2008 | Dumbauld et al. | |
| 7,445,621 B2 | 11/2008 | Dumbauld et al. | |
| 7,481,810 B2 | 1/2009 | Dumbauld et al. | |
| 7,491,201 B2 * | 2/2009 | Shields et al. | 606/51 |
| 7,500,975 B2 | 3/2009 | Cunningham et al. | |
| 7,540,872 B2 | 6/2009 | Schechter et al. | |
| 7,887,536 B2 | 2/2011 | Johnson et al. | |
| 7,951,150 B2 | 5/2011 | Johnson et al. | |
| 8,016,827 B2 | 9/2011 | Chojin | |
| 8,112,871 B2 | 2/2012 | Brandt et al. | |
| 8,114,122 B2 | 2/2012 | Nau, Jr. | |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,162,973 B2 | 4/2012 | Cunningham | |
| 8,187,273 B2 | 5/2012 | Kerr et al. | |
| 8,197,479 B2 | 6/2012 | Olson et al. | |
| 8,226,650 B2 | 7/2012 | Kerr | |
| 8,251,994 B2 | 8/2012 | McKenna et al. | |
| 8,257,387 B2 | 9/2012 | Cunningham | |
| 8,266,783 B2 | 9/2012 | Brandt et al. | |
| 2002/0115997 A1 | 8/2002 | Truckai et al. | |
| 2003/0018331 A1 | 1/2003 | Dycus et al. | |
| 2003/0229344 A1 | 12/2003 | Dycus et al. | |
| 2005/0096651 A1 | 5/2005 | Truckai et al. | |
| 2006/0064085 A1 | 3/2006 | Schechter et al. | |
| 2006/0074417 A1 | 4/2006 | Cunningham et al. | |
| 2006/0084973 A1 | 4/2006 | Hushka | |
| 2006/0129146 A1 | 6/2006 | Dycus et al. | |
| 2007/0043352 A1 | 2/2007 | Garrison et al. | |
| 2007/0043353 A1 | 2/2007 | Dycus et al. | |
| 2007/0062017 A1 | 3/2007 | Dycus et al. | |
| 2007/0078458 A1 | 4/2007 | Dumbauld et al. | |
| 2007/0088356 A1 | 4/2007 | Moses et al. | |
| 2007/0142833 A1 | 6/2007 | Dycus et al. | |
| 2007/0173814 A1 | 7/2007 | Hixson et al. | |
| 2007/0179499 A1 | 8/2007 | Garrison | |
| 2008/0015566 A1 * | 1/2008 | Livneh | 606/37 |
| 2008/0319442 A1 | 12/2008 | Unger et al. | |
| 2009/0012520 A1 | 1/2009 | Hixson et al. | |
| 2009/0138006 A1 | 5/2009 | Bales et al. | |
| 2009/0149854 A1 | 6/2009 | Cunningham et al. | |
| 2009/0182327 A1 | 7/2009 | Unger | |
| 2010/0016857 A1 | 1/2010 | McKenna et al. | |
| 2010/0023009 A1 | 1/2010 | Moses et al. | |
| 2010/0036375 A1 | 2/2010 | Regadas | |
| 2010/0042143 A1 | 2/2010 | Cunningham | |
| 2010/0049187 A1 | 2/2010 | Carlton et al. | |
| 2010/0057081 A1 | 3/2010 | Hanna | |
| 2010/0057082 A1 | 3/2010 | Hanna | |
| 2010/0057083 A1 | 3/2010 | Hanna | |
| 2010/0057084 A1 | 3/2010 | Hanna | |
| 2010/0063500 A1 | 3/2010 | Muszala | |
| 2010/0069903 A1 | 3/2010 | Allen, IV et al. | |
| 2010/0069904 A1 | 3/2010 | Cunningham | |
| 2010/0069953 A1 | 3/2010 | Cunningham | |
| 2010/0076427 A1 | 3/2010 | Heard | |
| 2010/0076430 A1 | 3/2010 | Romero | |
| 2010/0076431 A1 | 3/2010 | Allen, IV | |
| 2010/0076432 A1 | 3/2010 | Horner | |
| 2010/0087816 A1 | 4/2010 | Roy | |
| 2010/0094271 A1 | 4/2010 | Ward et al. | |
| 2010/0094287 A1 | 4/2010 | Cunningham et al. | |
| 2010/0100122 A1 | 4/2010 | Hinton | |
| 2010/0130971 A1 | 5/2010 | Baily | |
| 2010/0130977 A1 | 5/2010 | Garrison et al. | |
| 2010/0179543 A1 | 7/2010 | Johnson et al. | |
| 2010/0179545 A1 | 7/2010 | Twomey et al. | |
| 2010/0179546 A1 | 7/2010 | Cunningham | |
| 2010/0179547 A1 | 7/2010 | Cunningham et al. | |
| 2010/0249769 A1 | 9/2010 | Nau, Jr. et al. | |
| 2010/0274244 A1 | 10/2010 | Heard | |
| 2010/0280511 A1 | 11/2010 | Rachlin et al. | |
| 2011/0015632 A1 | 1/2011 | Artale | |
| 2011/0034918 A1 | 2/2011 | Reschke | |
| 2011/0046623 A1 | 2/2011 | Reschke | |
| 2011/0054467 A1 | 3/2011 | Mueller et al. | |
| 2011/0054468 A1 | 3/2011 | Dycus | |
| 2011/0054469 A1 | 3/2011 | Kappus et al. | |
| 2011/0054471 A1 | 3/2011 | Gerhardt et al. | |
| 2011/0054472 A1 | 3/2011 | Romero | |
| 2011/0060333 A1 | 3/2011 | Mueller | |
| 2011/0060334 A1 | 3/2011 | Brandt et al. | |
| 2011/0060335 A1 | 3/2011 | Harper et al. | |
| 2011/0071523 A1 | 3/2011 | Dickhans | |
| 2011/0077648 A1 | 3/2011 | Lee et al. | |
| 2011/0077649 A1 | 3/2011 | Kingsley | |
| 2011/0082457 A1 | 4/2011 | Kerr et al. | |
| 2011/0082494 A1 | 4/2011 | Kerr et al. | |
| 2011/0087221 A1 | 4/2011 | Siebrecht et al. | |
| 2011/0098689 A1 | 4/2011 | Nau, Jr. et al. | |
| 2011/0118736 A1 | 5/2011 | Harper et al. | |
| 2011/0184405 A1 | 7/2011 | Mueller | |
| 2011/0190653 A1 | 8/2011 | Harper et al. | |
| 2011/0190765 A1 | 8/2011 | Chojin | |
| 2011/0193608 A1 | 8/2011 | Krapohl | |
| 2011/0218530 A1 | 9/2011 | Reschke | |
| 2011/0230880 A1 | 9/2011 | Chojin et al. | |
| 2011/0238066 A1 | 9/2011 | Olson | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 202007009165 | 8/2007 |
| DE | 20 2007 009317 | 10/2007 |
| DE | 19738457 | 1/2009 |
| EP | 1159926 | 12/2001 |
| EP | 1 486 177 | 12/2004 |
| EP | 1 535 581 | 6/2005 |
| EP | 1 642 543 | 4/2006 |
| EP | 1 649 821 | 4/2006 |
| EP | 1810625 | 7/2007 |
| EP | 2243439 | 10/2010 |
| EP | 2294998 | 3/2011 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |

| | | |
|---|---|---|
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2004/073490 | 9/2004 |
| WO | WO 2005/004734 | 1/2005 |
| WO | WO 2005/004735 | 1/2005 |
| WO | WO 2005/110264 | 11/2005 |
| WO | WO 2006/021269 | 3/2006 |
| WO | WO2008008457 | 1/2008 |

OTHER PUBLICATIONS

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
European Search Report for European Application No. 11151509, dated Jun. 6, 2011.
Int'l Search Report EP 08 020807.7 dated Apr. 24, 2009.
Int'l Search Report EP 09 003677.3 dated May 4, 2009.
Int'l Search Report EP 09 005051.9 dated Jul. 6, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US03/18676 dated Sep. 19, 2003.
Int'l Search Report PCT/US08/52460 dated Apr. 24, 2008.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product. Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended- EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended- EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
International Search Report EP10175956 dated Nov. 12, 2010.

* cited by examiner

COMPACT JAW INCLUDING THROUGH BORE PIVOT PIN

BACKGROUND

1. Technical Field

The present disclosure relates to an apparatus for performing an endoscopic electrosurgical procedure. More particularly, the present disclosure relates to an apparatus for performing an endoscopic electrosurgical procedure that employs an endoscopic electrosurgical apparatus that includes an end effector assembly configured for use with variously-sized access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect homeostasis by heating the tissue and blood vessels to coagulate, cauterize, fuse, seal, cut, desiccate, and/or fulgurate tissue.

As an alternative to open electrosurgical forceps for use with open surgical procedures, many modern surgeons use endoscopes and endoscopic electrosurgical apparatus (e.g., endoscopic forceps) for remotely accessing organs through smaller, puncture-like incisions. As a direct result thereof, patients tend to benefit from less scarring, less pain, and reduced healing time. Typically, the endoscopic forceps are inserted into the patient through one or more various types of cannulas or access ports (typically having an opening that ranges from about five millimeters to about fifteen millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

Accordingly, the present disclosure is directed to an end effector assembly for use with a forceps. The end effector assembly includes a pair of jaw members, a knife assembly and one or more cam assemblies. One or both jaw members are moveable relative to the other about a pivot from a first, open position to a second, closed position for grasping tissue. The pivot includes a bore defined therethrough. One or both jaw members include a knife channel defined therein that extends therealong. One or both jaw members may be adapted to connect to an electrosurgical energy source to electrosurgically treat tissue. One or both jaw members may define one or more cam slots therein.

The knife assembly includes a knife blade and an actuation shaft. The knife blade is disposed distally relative to the pivot. The actuation shaft is configured for slidable translation through the bore defined in the pivot to allow selective advancement of the knife blade through the knife channel. The knife blade is affixed to a distal end of the actuation shaft.

The cam assemblies are operably coupled to one or both jaw members and are actuatable to move one or both jaw members from the first to second position for grasping tissue therebetween. The cam assemblies include an actuator configured to move one or both jaw members from the first to second position upon selective longitudinal translation thereof. An actuator bore is defined through the actuator that is configured to slidably receive the actuation shaft therethrough. The actuator includes one or more cam pins extending therefrom such that the cam slots of the jaw members and the one or more cam pins are configured to cooperate with one another.

In embodiments, the actuation shaft and one or both of the bore of the pivot and the actuator bore have non-circular cross-sections such that the actuation shaft and one or both of the bore of the pivot and the actuator bore cooperate to prevent the knife blade from rotating.

In one aspect, the forceps includes a housing, a pair of jaw members, a knife assembly, and one or more cam assemblies. The housing has a shaft that extends therefrom that includes a clevis at a distal end thereof. The pair of jaw members are mounted to the clevis about a pivot. One or both jaw members are moveable relative to the other about the pivot from a first, open position to a second, closed position for grasping tissue. One or both jaw members include a knife channel defined therein that extends therealong. The pivot includes a bore defined therethrough. The pivot may be fixedly connected to the clevis. One or both jaw members may be adapted to connect to an electrosurgical energy source to electrosurgically treat tissue. One or both jaw members may define one or more cam slots therein.

The knife assembly includes a knife blade and an actuation shaft. The knife blade is disposed distally relative to the pivot. The actuation shaft is configured for slidable translation through the bore defined in the pivot to allow selective advancement of the knife blade through the knife channel. The knife blade is affixed to a distal end of the actuation shaft.

The cam assemblies are operably coupled to one or both moveable jaw members and are actuatable to move one or both jaw members from the first to second position for grasping tissue therebetween. The cam assemblies include an actuator operably coupled to the housing that is configured to move one or both jaw members from the first to second position upon selective longitudinal translation thereof. The actuator may be moveable to actuate both jaw members. An actuator bore is defined through the actuator and is configured to slidably receive the actuation shaft therethrough. The actuator includes one or more cam pins extending therefrom such that the one or more cam slots of the jaw members and the one or more cam pins are configured to cooperate with one another.

In one embodiment, a knife tube is disposed through the one or more channels of the clevis and is dimensioned to slidingly receive a knife assembly therein. The knife assembly includes a knife blade and an actuation shaft. The knife blade is disposed distally relative to the pivot. The actuation shaft is configured for slidable translation through the knife tube and the bore of the pivot to allow selective advancement of the knife blade through the knife channel. The knife blade may be affixed to a distal end of the actuation shaft.

In embodiments, the actuation shaft and one or both of the bore of the pivot and the actuator bore have non-circular cross-sections such that the actuation shaft and one or both of the bore of the pivot and the actuator bore cooperate to prevent the knife blade from rotating.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaws from an open to a closed configuration that forms a closed loop electrical circuit such that a desired tissue effect (e.g., tissue seal) may be achieved.

Figure 1:
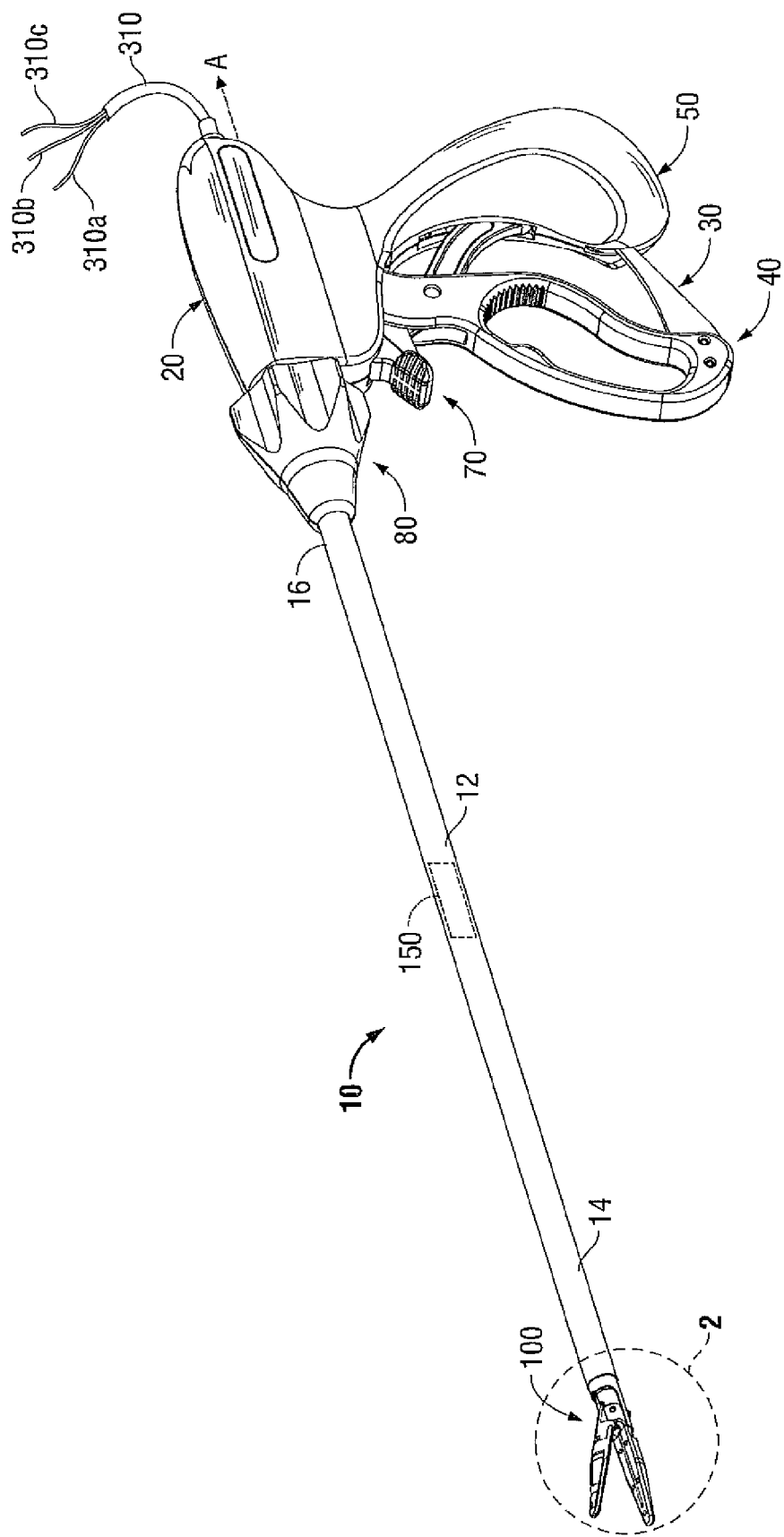
FIG. 1 is a right perspective view of an endoscopic bipolar forceps showing a housing, a shaft, and an end effector assembly in accordance with an embodiment of the present disclosure.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of a laparoscopic instrument; however, it is contemplated that an open version of the forceps may also include the same or similar operating components and features as described below.

Forceps 10 includes a shaft 12 that has a distal end 14 dimensioned to mechanically engage the end effector assembly 100 and a proximal end 16 that mechanically engages the housing 20. In the drawings and in the descriptions that follow, the term "proximal" as is traditional, will refer to the end of the forceps 10 that is closer to the user, while the term "distal" will refer to the end that is further from the user.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033,399 entitled "ELECTROSURGICAL GENERATOR WITH ADAPTIVE POWER CONTROL". Cable 310 is internally divided into cable leads 310a, 310b, and 310c, which are designed to transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly owned Patent Publication No. 2003-0229344, filed on Feb. 20, 2003, entitled VESSEL SEALER AND DIVIDER AND METHOD OF MANUFACTURING THE SAME.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A" (See FIG. 1).

As mentioned above, end effector assembly 100 is attached at the distal end 14 of shaft 12 and includes a pair of opposing jaw members 110 and 120. Movable handle 40 of handle assembly 30 is operatively connected to a suitable drive assembly 150 (shown in phantom) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, drive assembly 150 may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

Figure 2:
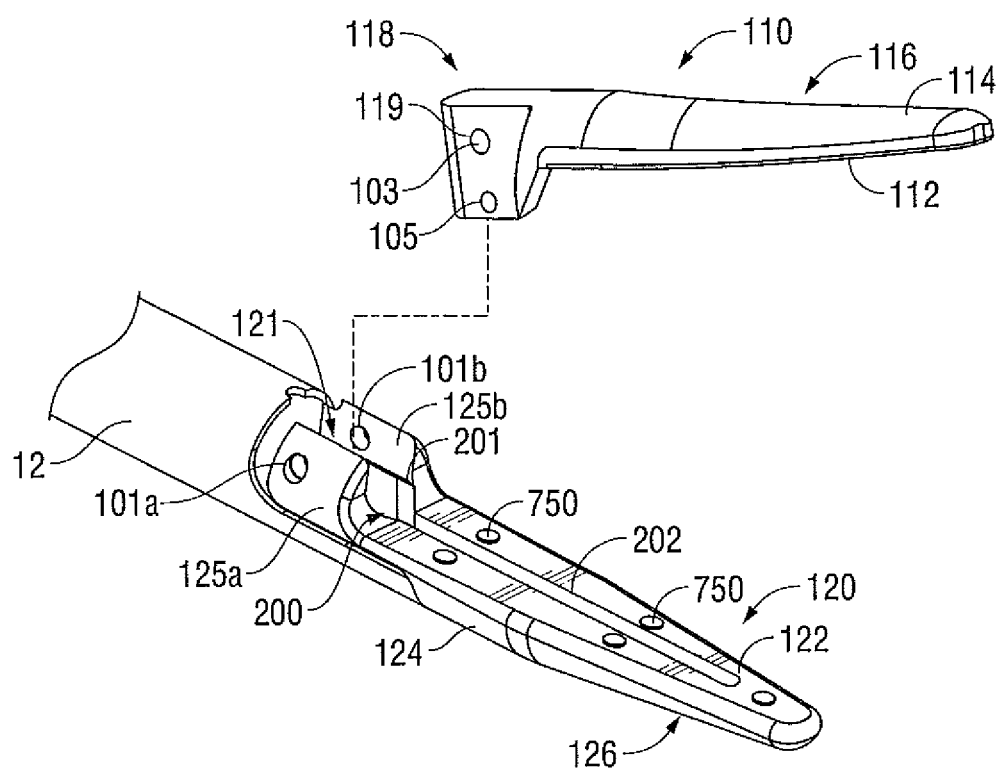
FIG. 2 is an enlarged, left perspective view of the end effector assembly of FIG. 1 with the jaw members shown in open configuration.
Figure 3A:
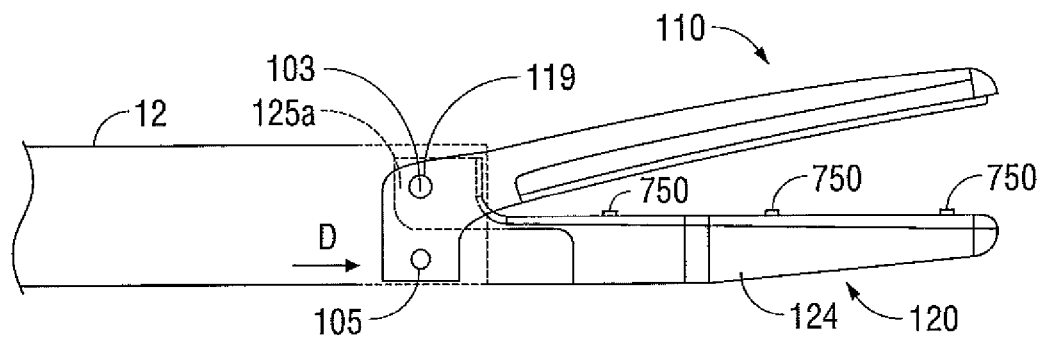
FIG. 3A is an enlarged, side view of the end effector assembly of FIG. 1 with the jaw members shown in open configuration.
Figure 3B:
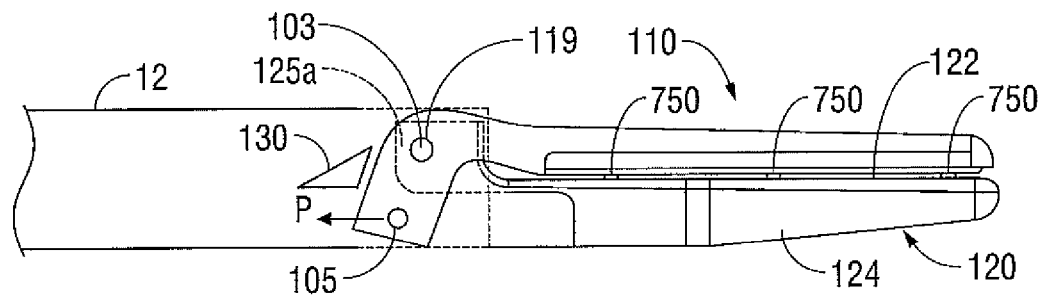
FIG. 3B is an enlarged, side view of the end effector assembly of FIG. 1 with the jaw members shown in closed configuration.

As shown best in FIGS. 2, 3A, and 3B, the end effector assembly 100 includes opposing jaw members 110 and 120 that cooperate to effectively grasp tissue for sealing purposes. The end effector assembly 100 may be designed as a unilateral assembly, i.e., jaw member 120 is fixed relative to the shaft 12 and jaw member 110 pivots about a pivot pin 103 relative to jaw member 120 to grasp tissue, or as a bilateral assembly, i.e., jaw members 110 and 120 pivot about pivot pin 103 relative to each other to grasp tissue. In some embodiments, and as will be discussed in further detail below, jaw members 110, 120 are operably coupled to each other via pivot pin 103 about which pivoting jaw member 110 pivots relative to stationary jaw member 120.

In the illustrated embodiment, the unilateral end effector assembly 100 includes one stationary or fixed jaw member 120 mounted in fixed relation to the shaft 12 and a pivoting jaw member 110 mounted about a pivot pin 103 attached to the stationary jaw member 120. In some embodiments, fixed jaw member 120 may be monolithically formed with shaft 12, e.g., stationary jaw member 120 may be defined by the distal end 14 of shaft 12.

Referring now to FIG. 2, jaw member 110 includes a pivot flange 118 having a mechanical interface 105 disposed thereon. Mechanical interface 105 may be, without limitation, a link, a gear, a pin, a rod, any combination thereof, or any interface suitable to operably couple pivot flange 118 to drive assembly 150, as will be discussed in further detail below. Pivot flange 118 also includes a pin slot 119 which is configured to engage pivot pin 103 to allow jaw member 110 to rotate relative to jaw member 120. More particularly, jaw member 120 includes a pair of proximal, upwardly extending flanges 125a and 125b which define a cavity 121 dimensioned to receive flange 118 of movable jaw member 110 therein. Each of the flanges 125a and 125b includes an aperture 101a and 101b, respectively, defined therethrough that secures pivot pin 103 on opposite sides of pivot mount 119 disposed within jaw member 110. As explained in further detail below, proximal movement of the drive assembly 150 engages mechanical interface 105 to pivot jaw member 110 to a closed position.

As best shown in FIGS. 3A and 3B, mechanical interface 105 is operable by the drive assembly 150 such that drive assembly 150 urges mechanical interface 105 in the distal and proximal directions, as indicated by directional arrows "D" and "P", respectively. The pivoting jaw member 110 is actuated by the drive assembly 150 such that the pivoting jaw member 110 pivots about pivot pin 103 between open and closed positions. Pulling the mechanical interface 105 proximally closes the jaw members 110 and 120 about tissue grasped therebetween and pushing the mechanical interface 105 distally opens the jaw members 110 and 120 for grasping purposes. In another embodiment, illustrated in FIG. 3C, pivot pin 103 is configured to slide within a cam slot to pivot jaw member 110 between open and closed positions.

As best shown in FIG. 2, jaw member 110 also includes a jaw housing 116 which has an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 are configured to limit and/or reduce many of the known undesirable effects related to tissue sealing, e.g., flashover, thermal spread and stray current dissipation. In other embodiments, the jaw members 110 and 120 may be manufactured from a ceramic-like material and the electrically conductive surface(s) 112 are coated onto the ceramic-like jaw members 110 and 120.

Jaw member 120 includes similar elements to jaw member 110 such as jaw housing 126 having an insulator 124 and an electrically conductive sealing surface 122 that is dimensioned to securely engage the insulator 124.

As best shown in FIG. 2, jaw member 120 may include a series of stop members 750 disposed on the inner facing surfaces of the electrically conductive sealing surface 122 to facilitate gripping and manipulation of tissue and to define a gap "G" (FIG. 4) between opposing jaw members 110 and 120 during sealing and cutting of tissue. As best shown in FIGS. 3A and 3B, pivoting jaw member 110 pivots about pivot pin 103 to the closed position such that conductive sealing surface 112 engages stop members 750. Once end effector assembly 100 is in the closed position and pivoting jaw member 110 is engaged with stop members 750 (FIG. 3B), movable handle 40 may be squeezed relative to stationary handle 50 to vary and/or generate additional closure pressure between jaw member 110 and stop members 750 for purposes of sealing tissue. The series of stop members 750 may be employed on one or both jaw members 110 and 120 depending upon a particular purpose or to achieve a desired result. A detailed discussion of stop members 750 as well as various manufacturing and assembling processes for attaching and/or affixing the stop members 750 to the electrically conductive sealing surfaces 112, 122 are described in commonly owned, co-pending U.S. Patent Publication Application No. 20040122423 entitled "VESSEL SEALER AND DIVIDER WITH NON-CONDUCTIVE STOP MEMBERS" by Dycus et al.

Figure 3C:
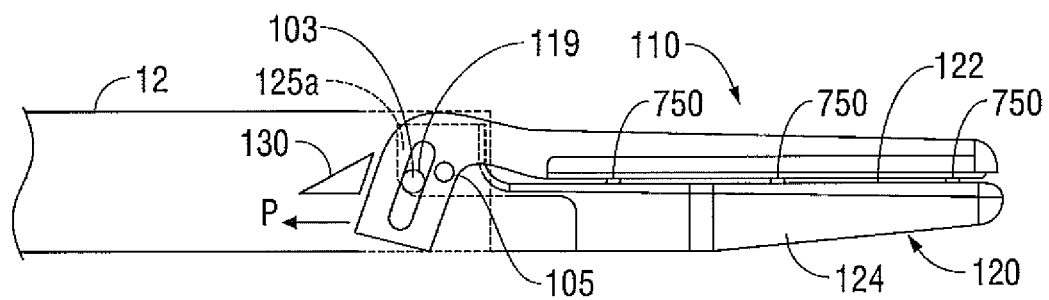
FIG. 3C is an enlarged, side view of an end effector assembly according to one embodiment of the present disclosure.

In some embodiments, as illustrated in FIGS. 3B and 3C, forceps 10 includes a camming member 130 disposed within shaft 12 and positioned to engage pivoting jaw member 110 at flange 118 when pivoting jaw member 110 is pivoted to the closed position. More specifically, as pivoting jaw member 110 pivots about pivot pin 103 from the open position to the closed position, i.e., in a clock-wise direction, camming member 130 cams a surface of flange 118 to prevent further pivoting of jaw member 110 about pivot pin 103 in the clockwise direction. Once end effector assembly 100 is in the closed position, and camming member 130 is engaged with flange 118, movable handle 40 may be squeezed relative to stationary handle 50 to vary and/or generate additional closure pressure between jaw members 110 and 120 and/or between jaw member 110 and stop members 750, as discussed hereinabove.

Figure 3D:
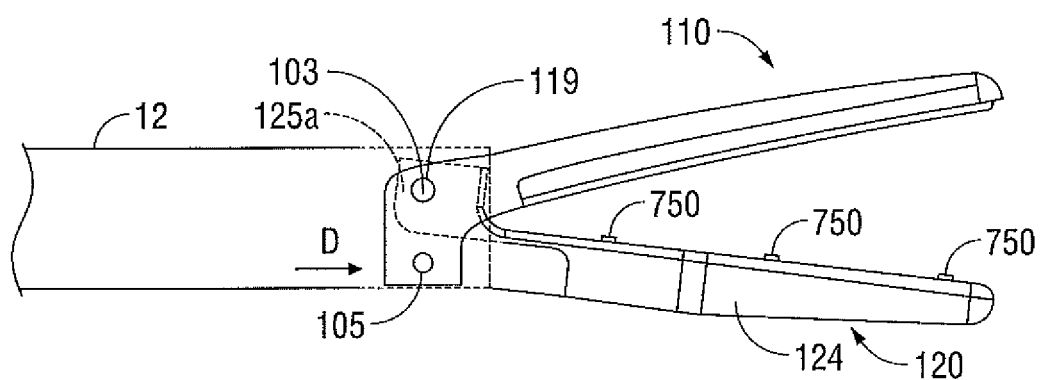
FIG. 3D is an enlarged, side view of an end effector assembly according to another embodiment of the present disclosure.

In some embodiments, as illustrated in FIG. 3D, the end effector assembly 100 may be designed as a bilateral assembly, i.e., each of jaw members 110 and 120 pivot about pivot pin 103 relative to each other to grasp tissue.

In the illustrated embodiment, the unilateral end effector assembly 100 includes one stationary or fixed jaw member 120 mounted in fixed relation to the shaft 12 and a pivoting jaw member 110 mounted about a pivot pin 103 attached to the stationary jaw member 120. In some embodiments, fixed jaw member 120 may be monolithically formed with shaft 12, e.g., stationary jaw member 120 may be defined by the distal end 14 of shaft 12.

Figure 4:
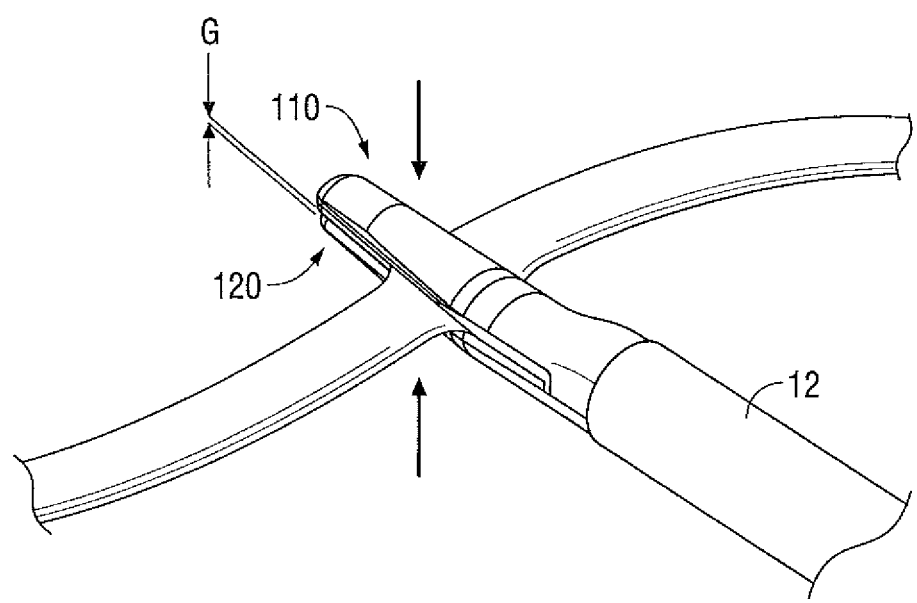
FIG. 4 is an enlarged, rear, perspective view of the end effectors shown grasping tissue.
Figure 5:
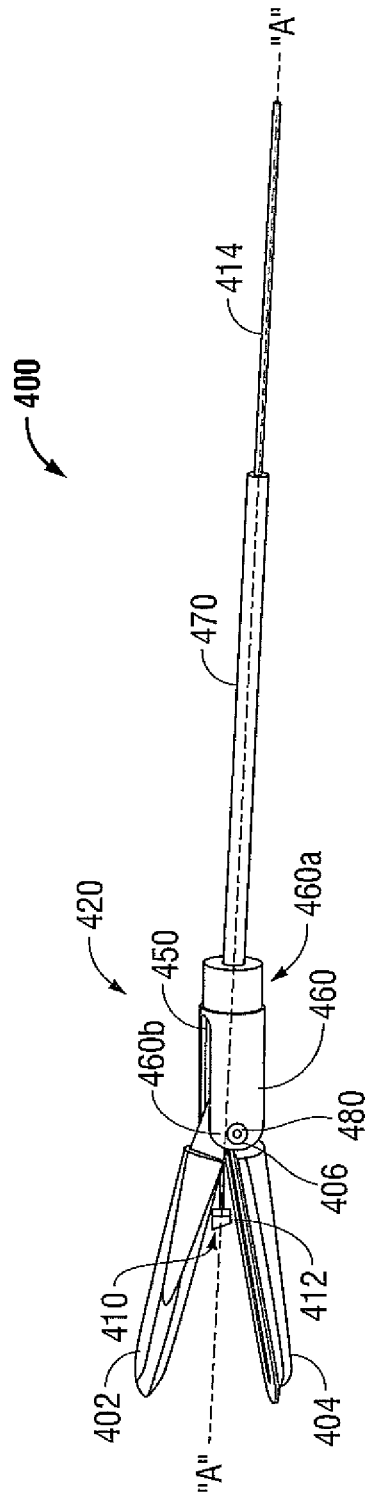
FIG. 5 is right, perspective view of an end effector assembly according to one embodiment of the present disclosure.

FIG. 4 shows the forceps grasping tissue. As the handle 40 is squeezed, the mechanical interface 105 is pulled proximally by the movement of drive assembly 150 to rotate flange 118 clock-wise which, in turn, pivots jaw member 110 about pivot pin 103 to the closed position.

The mechanical advantage realized from the jaw member 110, as discussed hereinabove, will enable the operator to impart an additional load on the drive assembly 150 by squeezing handle 40 (e.g., through use of an operably coupled torsion spring). The drive assembly's 150 load is converted to a torque about the jaw pivot 103. As a result, a specific closure force can be transmitted to the opposing jaw members 110 and 120. Each jaw member 110, 120 may be formed from material having malleable or flexible properties to provide a mechanical advantage. Further, the jaw members 110 and 120 may be opened, closed and rotated to manipulate tissue until sealing is desired. This enables the user to position and reposition the forceps 10 prior to activation and sealing.

Once jaws members 110 and 120 are fully compressed about the tissue, the forceps 10 are now ready for selective application of electrosurgical energy and subsequent separation of the tissue.

The mechanical advantage provided by one or both jaw members 110 and 120 facilitates and assures consistent, uniform and accurate closure pressure about tissue within the desired working pressure range of about 3 kg/cm$^2$ to about 16 kg/cm$^2$ in one embodiment and, in another embodiment, about 7 kg/cm$^2$ to about 13 kg/cm$^2$. By controlling the intensity, frequency and duration of the electrosurgical energy applied to tissue, the operator can either cauterize, coagulate/desiccate, seal and/or simply reduce or slow bleeding. Two mechanical factors play an important role in determining the resulting thickness of the seated tissue and effectiveness of the seal, i.e., the pressure applied between opposing jaw members 110 and 120 and the gap distance "G" between the opposing sealing surfaces 112, 122 of the jaw members 110 and 120 during the sealing process.

As mentioned above, one or both jaw members, 110, 120 may include a stop member 750 which limits the movement of the two opposing jaw members 110 and 120 relative to one another. The stop member 750 extends from the sealing surface 122 a predetermined distance according to the specific material properties (e.g., compressive strength, thermal expansion, etc.) to yield a consistent and accurate gap distance "G" during sealing (FIG. 4). In embodiments, the gap distance between opposing sealing surfaces 112 and 122 during sealing ranges from about 0.001 inches to about 0.006 inches and, in other embodiments, between about 0.002 and about 0.003 inches. The non-conductive stop members 750 may be, without limitation, molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several suitable thermal spraying techniques may be utilized including, for example, depositing a broad range of heat resistant and insulative materials on various surfaces to create stop members 750 for controlling the gap distance between electrically conductive surfaces 112 and 122.

As shown in FIG. 2, the present disclosure may incorporate a knife assembly 200 that, when activated via the trigger assembly 70, progressively and selectively divides tissue along a tissue plane in a precise manner to effectively and reliably divide the tissue. The knife assembly 200 includes a knife blade 201 and a knife channel 202 extending along either one or both of the jaw members 110, 120. The knife blade 201 is configured for selective translation within the knife channel 202.

Referring again to FIG. 2, the knife blade 201 is disposed in a first position, which is an unactuated position. Upon actuation of the trigger assembly 70, the knife blade 201 of the knife assembly 200 translates through the knife channel 202.

Referring now to FIGS. 5-9, one embodiment of an end effector assembly 400 for use with forceps 10 includes a cam assembly 420, a pair of jaw members 402, 404, a knife assembly 410, and a knife tube 470.

Figure 8:
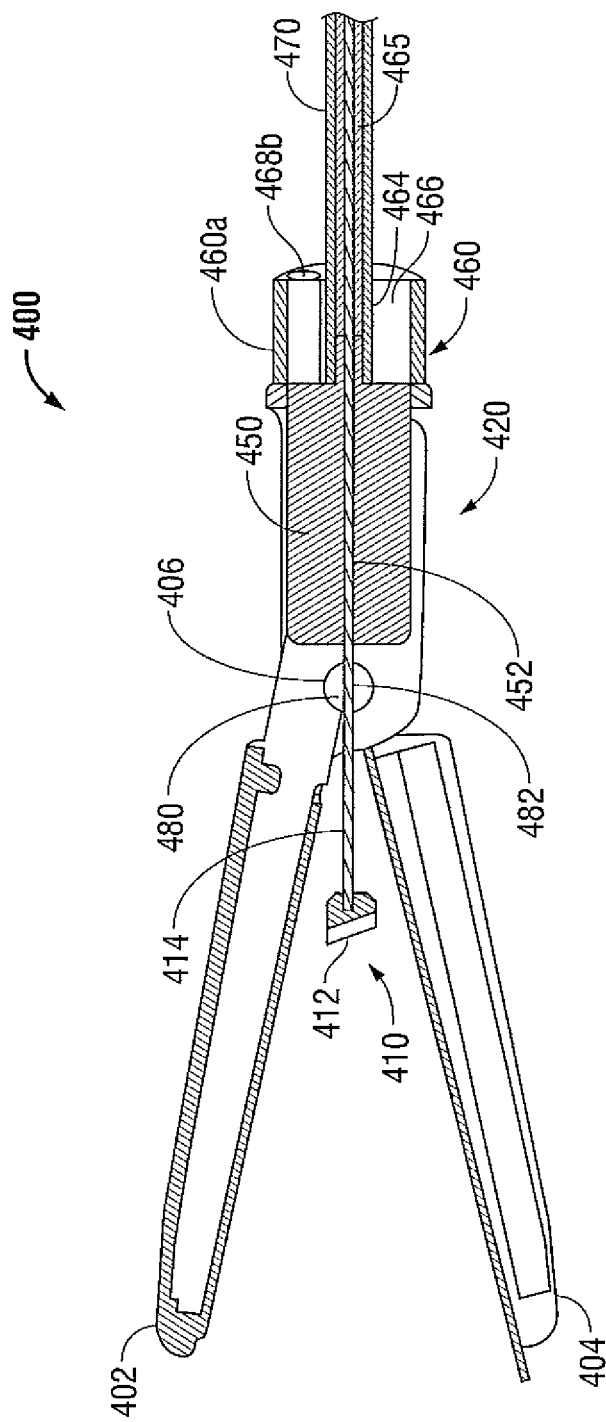
FIG. 8 is an enlarged, right, cross-sectional view of the end effector assembly of FIG. 5.
Figure 9:
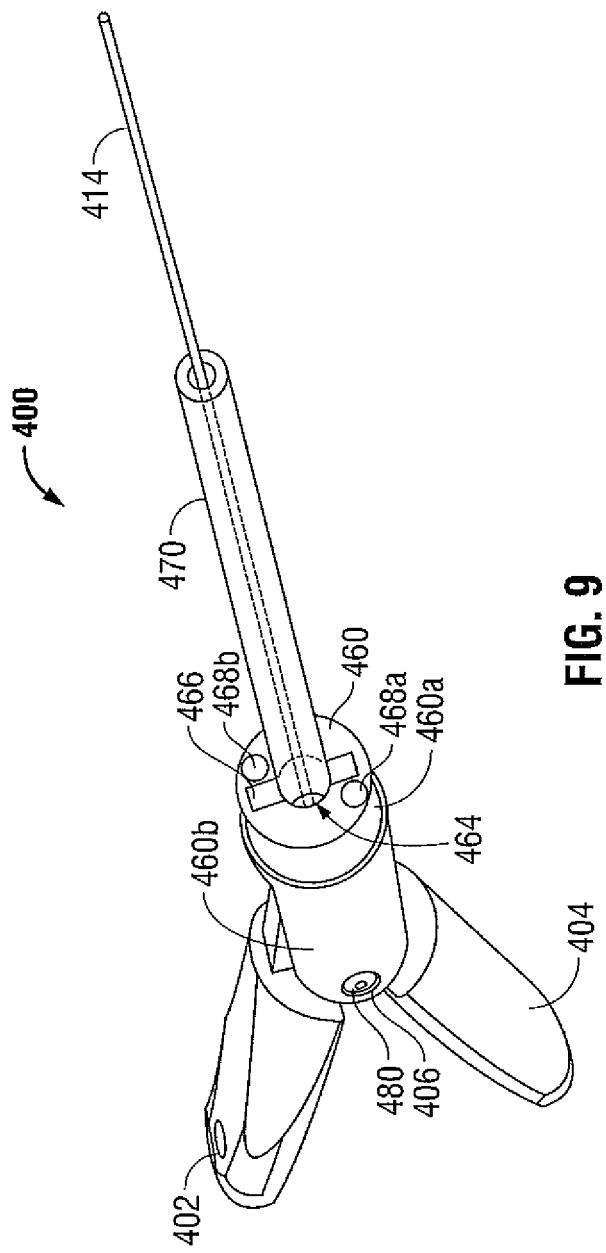
FIG. 9 is an enlarged, right, rear, perspective view of the end effector assembly of FIG. 5.

As best shown in FIG. 8, the cam assembly 420 includes an actuator 450, a pivot 480, a clevis 460, and a knife tube 470. One or both jaw members 402, 404 are moveable relative to the other about the pivot 480 from a first, open position to a second, closed position for grasping tissue. The pivot 480 includes a bore 482 defined therethrough for slidably receiving the knife assembly 410 therethrough. The bore 482 may have any suitable cross-sectional shape (e.g., circular or non-circular). The clevis 460 and the jaw members 402, 404 are operably coupled by the pivot 480 which is mounted via a pivot bore 406 defined through the clevis 460 and jaw members 402, 404. The pair of jaw members 402, 404 are mounted to the clevis 460 at the distal end 460b of the clevis 460. The pivot 480 may be fixedly connected to the clevis 460. The knife tube 470 is operably coupled to the clevis 460 via a knife tube channel 464 defined in the proximal end 460a of the clevis 460 such that the knife tube 470 slidably translates therethrough. The clevis 460 further includes an actuator channel 466 defined therethrough and disposed in vertical registration with knife tube channel 464. With reference to FIG. 9, cable channels 468a, 468b, etc. may also be defined through clevis 460 for receiving electrosurgical cable leads 310a, 310b, etc. (FIG. 1) therethrough.

Figure 6:
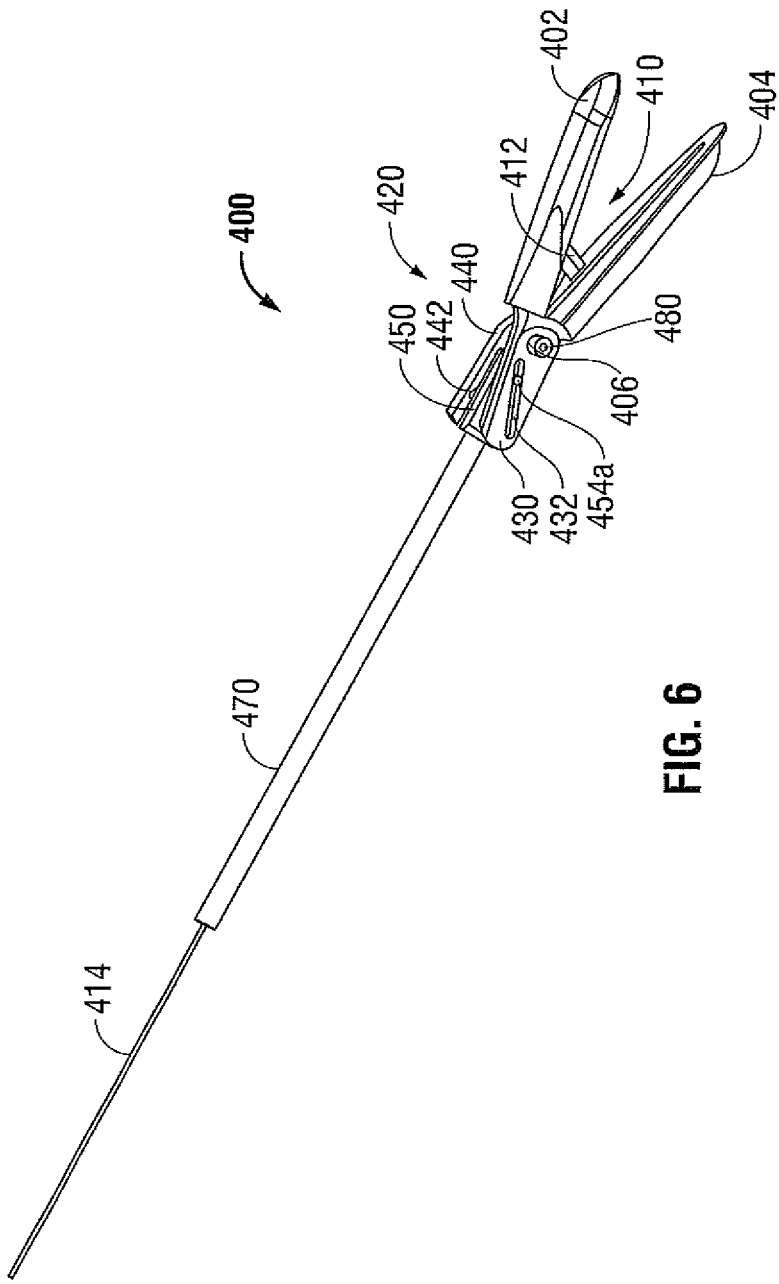
FIG. 6 is a left, perspective view of the end effector assembly of FIG. 5 with a clevis removed for clarity.

From FIG. 6, the pair of jaw members 402, 404 include cam portions 430, 440 at the proximal end thereof. Each cam portion 430, 440 of the respective jaw member 402, 404 is actuatable by the actuator 450 to move one or both jaw members 402, 404 from a first to a second position upon selective longitudinal translation thereof for grasping tissue therebetween. Cam portions 430, 440 of jaw members 402, 404 include cam slots 432, 442 defined therein that are configured to cooperate with one or more corresponding cam pins 454a, 454b (FIG. 7) extending from the actuator 450 to actuate one or both jaw members 402, 404. Each cam slot 432, 442 is disposed in opposed angular relation relative to one another.

The knife tube 470 is disposed in mechanical cooperation with the actuator 450 and mounted to the shaft 12 of the forceps 10. The knife tube 470 may be rigidly attached to the actuator 450. As illustrated in FIG. 8, a liner 465 may be mounted within knife tube 470 for limiting splay of the actuation shaft 414 as the actuation shaft translates through the knife tube 470. The knife tube 470 is operably associated with the drive assembly 150 thereof for longitudinally translating the knife tube 470. The knife tube 470 is configured to slidingly receive the knife assembly 410 therein.

Referring again to FIGS. 5, 6 and 8, the knife assembly 410 includes a knife blade 412 and an actuation shaft 414. The actuation shaft 414 may have any suitable cross-sectional shape (e.g., circular or noncircular). In one embodiment, the actuation shaft 414 is formed with an indexing profile (e.g., square) in cooperation with a substantially similarly shaped bore 482 to prevent rotational movement of the knife blade 412. The actuation shaft 414 is operably associated with the trigger assembly 70 of forceps 10 (FIG. 1). The knife blade 412 is disposed distal to the pivot 480. The actuation shaft 414 is configured for slidable translation through the knife tube 470 and the bore 482 of the pivot 480 to allow selective advancement of the knife blade 412 through the knife channel 202 of the jaw members 402, 404 upon activation by the trigger assembly 70. An actuator bore 452 (FIG. 8) may be defined through the actuator 450 for slidably receiving actuation shaft 414 therethrough. Like the actuation shaft 414 and the bore 482, the actuator bore 452 may have any suitable cross-sectional shape (e.g., circular or non-circular) for cooperating with the actuation shaft 414 to prevent rotational movement of the knife blade 412. The knife blade 412 may be affixed to a distal end of the actuation shaft 414.

Figure 7:
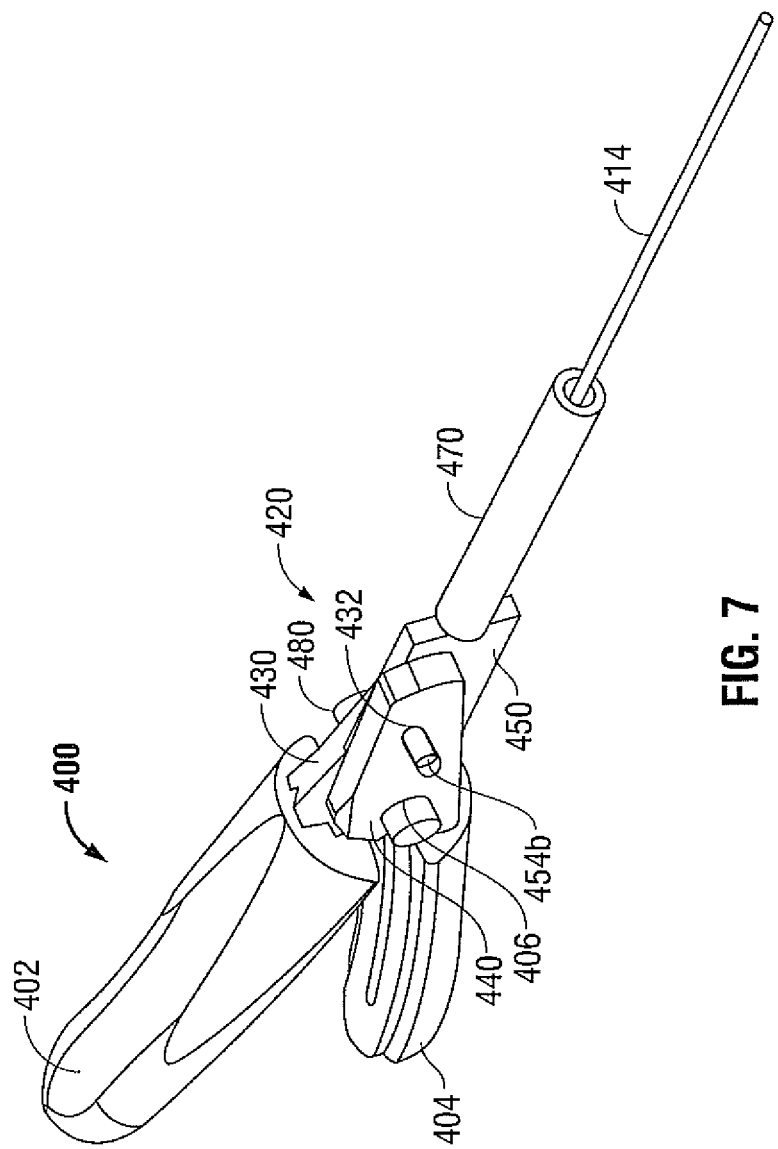
FIG. 7 is an enlarged, right, rear, perspective view of FIG. 6.

In operation, upon actuation of the movable handle 40, the drive assembly 150 slidably longitudinally translates the knife tube 470 through the knife tube channel 464 of the clevis 460. The knife tube 470 effectuates the longitudinal translation of the actuator 450 through the actuator channel 466 of the clevis 460. As the actuator 450 translates, each cam pin 454a, 454b slides within each respective cam slot 432, 442. As best shown in FIG. 7, when each cam pin 454a, 454b translates through each respective cam slot 432, 442, each cam 430, 440 vertically articulates about longitudinal axis "A" (FIG. 5) in opposing direction to the other. In effect, each respective jaw member 402, 404 rotates about the pivot 480 in response to the longitudinal translation of the actuator 450. Upon actuation of the trigger assembly 70, the actuation shaft 414 translates through the knife tube 470, the actuator bore 452, and the bore 482 of the pivot 480 for advancing the knife blade 412 through the knife channel 202 of the jaw members 402, 404.

With this embodiment, the distance to the pivot point is significantly reduced which facilitates assembly and ease of use. In certain embodiments, this shortened distance to the pivot point facilitates articulation of the end effector.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for use with a forceps, the end effector assembly comprising:
a clevis supporting a pair of jaw members and a pivot, the clevis having a proximal end face and defining a clevis bore with a non-circular cross-section that extends longitudinally through the clevis from the proximal end face of the clevis, the clevis bore configured to receive an actuator that moves at least one jaw member of the pair of jaw members relative to the other about the pivot from a first, open position to a second, closed position for grasping tissue, at least one of the jaw members including a knife channel defined therein that extends therealong, the pivot defining a pivot bore therethrough;
a knife assembly including a knife blade and an actuation shaft, the knife blade disposed distally relative to the pivot, the actuation shaft configured for slidable translation through the pivot bore to allow selective advancement of the knife blade through the knife channel; and
at least one cam assembly operably coupled to the at least one jaw member and actuatable by the actuator to move the at least one jaw member from the first position to the second position for grasping tissue between the pair of jaw members.

2. The end effector assembly according to claim 1, wherein the actuator is configured to move the at least one movable jaw member from the first to second position upon selective longitudinal translation of the actuator.

3. The end effector assembly according to claim 2, wherein the actuator includes at least one cam pin extending therefrom and wherein at least one jaw member defines at least one cam slot therein such that the at least one cam slot and the at least one cam pin are configured to cooperate with one another.

4. The end effector assembly according to claim 2, wherein an actuator bore is defined through the actuator that is configured to slidably receive the actuation shaft therethrough.

5. The end effector assembly according to claim 4, wherein the actuation shaft, the pivot bore, and the actuator bore have non-circular cross-sections such that the actuation shaft, one of the pivot bore, and the actuator bore cooperate to prevent the knife blade from rotating.

6. The end effector assembly according to claim 1, wherein the knife blade is affixed to a distal end of the actuation shaft.

7. The end effector assembly according to claim 1, wherein at least one of the jaw members is adapted to connect to an electrosurgical energy source to electrosurgically treat tissue.

8. A forceps, comprising:
a housing having a shaft that extends therefrom, the shaft supporting that includes a clevis at a distal end thereof and an actuator, the clevis having a proximal end face and defining a clevis bore with a non-circular cross-section that extends longitudinally through the clevis from the proximal end face of the clevis;
a pair of jaw members mounted to the clevis about a pivot, at least one jaw member moveable relative to the other about the pivot from a first, open position to a second, closed position for grasping tissue between the pair of jaw members, at least one of the jaw members including a knife channel defined therein that extends therealong, the pivot defining a pivot bore therethrough;
a knife assembly including a knife blade and an actuation shaft, the knife blade disposed distally relative to the pivot and the actuation shaft configured for slidable translation through the pivot bore to allow selective advancement of the knife blade through the knife channel; and
at least one cam assembly operably coupled to the at least one moveable jaw member and actuatable in response to movement of the actuator through the clevis bore to move the at least one jaw member from the first to second position for grasping tissue between the pair of jaw members.

9. The forceps according to claim 8, wherein the actuator is operably coupled to the housing and is configured to move the at least one jaw member from the first to second position upon selective longitudinal translation of the actuator through the clevis bore thereof.

10. The forceps according to claim 9, wherein the actuator includes at least one cam pin extending therefrom and wherein at least one jaw member defines at least one cam slot therein such that the at least one cam slot and the at least one cam pin are configured to cooperate with one another.

11. The forceps according to claim 9, wherein an actuator bore is defined through the actuator, the actuator bore configured to slidably receive the actuation shaft therethrough.

12. The forceps according to claim 11, wherein the actuation shaft, the pivot bore, and the actuator bore have non-circular cross-sections such that the actuation shaft, the pivot bore, and the actuator bore cooperate to prevent the knife blade from rotating.

13. The forceps according to claim 9, wherein the actuator is moveable to actuate both jaw members.

14. The forceps according to claim 8, wherein the knife blade is affixed to a distal end of the actuation shaft.

15. The forceps according to claim 8, wherein at least one of the jaw members is adapted to connect to an electrosurgical energy source to electrosurgically treat tissue.

16. The forceps according to claim 8, wherein the pivot is fixedly connected to the clevis.

17. A forceps, comprising:
a housing having a shaft that extends therefrom, the shaft supporting a clevis at a distal end thereof and an actuator, the clevis defining a clevis bore with a non-circular cross-section that extends longitudinally through the clevis from a proximal end thereof for the reception of the actuator;
a pair of jaw members mounted to the clevis about a pivot, at least one jaw member moveable relative to the other about the pivot from a first, open position to a second, closed position for grasping tissue between the pair of jaw members, at least one of the jaw members including a knife channel defined therein that extends therealong, the pivot defining a pivot therethrough;

a knife tube secured to the actuator and positionable within the clevis bore, the knife tube configured and dimensioned to slidingly receive a knife assembly therein, the knife assembly including a knife blade and an actuation shaft, the knife blade disposed distally relative to the pivot, the actuation shaft configured for slidable translation through the knife tube and the pivot bore to allow selective advancement of the knife blade through the knife channel; and at least one cam assembly operably coupled to the at least one jaw member and actuatable in response to movement of the actuator through the clevis bore to move the at least one jaw member from the first to second position for grasping tissue between the pair of jaw members.

18. The forceps according to claim 17, wherein the actuator is operably coupled to the housing and is configured to move the at least one jaw member from the first to second position upon selective longitudinal translation of the actuator through the clevis bore.

19. The forceps according to claim 18, wherein the actuator includes at least one cam pin extending therefrom and wherein at least one jaw member defines at least one cam slot therein such that the at least one cam slot and the at least one cam pin are configured to cooperate with one another.

20. The forceps according to claim 17, wherein the knife blade is affixed to a distal end of the actuation shaft.

21. The forceps according to claim 17, wherein at least one of the jaw members is adapted to connect to an electrosurgical energy source to electrosurgically treat tissue.

22. The forceps according to claim 17, wherein the pivot is fixedly connected to the clevis.

23. The forceps according to claim 17, wherein the actuation shaft and the pivot bore have non-circular cross-sections such that the actuation shaft and the pivot bore cooperate to prevent the knife blade from rotating.

* * * * *